(12) United States Patent
Jugl et al.

(10) Patent No.: US 10,130,773 B2
(45) Date of Patent: Nov. 20, 2018

(54) ASSEMBLY FOR A DRUG DELIVERY DEVICE

(71) Applicant: Sanofi-Aventis Deutschland GMBH, Frankfurt am Main (DE)

(72) Inventors: Michael Jugl, Frankfurt am Main (DE); Axel Teucher, Frankfurt am Main (DE)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 129 days.

(21) Appl. No.: 15/109,487

(22) PCT Filed: Dec. 23, 2014

(86) PCT No.: PCT/EP2014/079253
§ 371 (c)(1),
(2) Date: Jul. 1, 2016

(87) PCT Pub. No.: WO2015/101574
PCT Pub. Date: Jul. 9, 2015

(65) Prior Publication Data
US 2016/0325049 A1    Nov. 10, 2016

(30) Foreign Application Priority Data
Jan. 2, 2014    (EP) ................................... 14150066

(51) Int. Cl.
*A61M 5/00* (2006.01)
*A61M 5/315* (2006.01)
*A61M 5/31* (2006.01)

(52) U.S. Cl.
CPC .... *A61M 5/31555* (2013.01); *A61M 5/31566* (2013.01); *A61M 5/31575* (2013.01);
(Continued)

(58) Field of Classification Search
CPC ...... A61M 2205/581; A61M 2205/582; A61M 2205/583; A61M 5/3146; A61M 5/31555;
(Continued)

(56) References Cited

U.S. PATENT DOCUMENTS

| | | | |
|---|---|---|---|
| 2012/0109074 A1 | 5/2012 | Oakland | |
| 2014/0025016 A1* | 1/2014 | Plumptre | A61M 5/24 604/209 |

FOREIGN PATENT DOCUMENTS

WO    WO2012/130705    10/2012

OTHER PUBLICATIONS

International Search Report and Written Opinion in International Application No. PCT/EP2014/079253, dated Mar. 20, 2015, 10 pages.
(Continued)

*Primary Examiner* — Rebecca E Eisenberg
(74) *Attorney, Agent, or Firm* — Fish & Richardson P.C.

(57) ABSTRACT

An assembly for a drug delivery device (1) is provided, the assembly comprising a piston rod (10) and a force transfer subassembly (16, 17), the force transfer subassembly being arranged and configured, in a driving mode of operation of the assembly, to transfer a driving force (F) to the piston rod in order to drive the piston rod, the force transfer subassembly comprising a first force transfer member (17), and a second force transfer member (16), wherein the first force transfer member and the second force transfer member are operatively coupled to each other via a force-sensitive coupling (27) to transfer the driving force to the piston rod, and wherein, when an excessive force acts on the force-sensitive coupling, the force-sensitive coupling is arranged and configured to be released in order to switch the assembly from the driving mode of operation into a security mode of operation.

17 Claims, 5 Drawing Sheets

(52) U.S. Cl.
CPC .... *A61M 5/31585* (2013.01); *A61M 5/31593* (2013.01); *A61M 5/3146* (2013.01); *A61M 2205/581* (2013.01); *A61M 2205/582* (2013.01); *A61M 2205/583* (2013.01); *A61M 2207/00* (2013.01)

(58) Field of Classification Search
CPC .......... A61M 5/31566; A61M 5/31575; A61M 5/31585; A61M 5/31593
See application file for complete search history.

(56) References Cited

OTHER PUBLICATIONS

International Preliminary Report on Patentability in International Application No. PCT/EP2014/079253, dated Jul. 5, 2016, 8 pages.
Rote Liste, "50. Hypophysen–, Hypothalamushormone, andere regulatorische Peptide u. ihre Hemmstoffe," Chapter 50, ed. 2008, 20 pages.

* cited by examiner

ASSEMBLY FOR A DRUG DELIVERY DEVICE

CROSS-REFERENCE TO RELATED APPLICATIONS

This application is a U.S. national stage application under 35 USC § 371 of International Application No. PCT/EP2014/079253, filed on Dec. 23, 2014, which claims priority to European Patent Application No. 14150066.0, filed on Jan. 2, 2014, the entire contents of which are incorporated herein by reference.

The present disclosure relates to an assembly for a drug delivery device and to a drug delivery device comprising the assembly.

In drug delivery devices a force is usually transferred to an element which is provided to drive a dispensing movement in order to dispense drug from the device.

Certain aspects of the present invention relate to an assembly which facilitates provision of an improved drug delivery device.

One aspect of the present disclosure relates to an assembly for a drug delivery device. Another aspect of the present disclosure relates to a drug delivery device comprising the assembly. Consequently, features described herein in connection with the assembly or the drug delivery device are also disclosed with respect to the other one of the drug delivery device and the assembly. Likewise, features described in conjunction with different embodiments may also be applied in or combined with the ones of one or more other embodiments.

In an embodiment, the drug delivery device, in addition to the assembly, expediently comprises a reservoir, such as a cartridge, comprising the drug. The cartridge expediently comprises a movable piston or bung, which is movably retained within the cartridge, where movement of the piston with respect to the cartridge causes the drug to be dispensed from the cartridge. The drug may be a liquid drug.

In an embodiment, the assembly comprises a force transfer subassembly. The force transfer subassembly is preferably arranged and configured to transfer a driving force within the assembly, particularly in a driving mode of operation of the assembly. The driving force may be used to drive a dispensing action to dispense drug from the drug delivery device. The force transfer subassembly may be arranged and configured to transfer a setting force within the assembly, i.e. a force which is transferred within the assembly to move components during a dose setting action which may have to be performed before the dispensing action can be performed.

In an embodiment, the assembly comprises a piston rod. The piston rod may be arranged to be moved to drive dispensing of the drug from the drug delivery device. The force transfer subassembly may be arranged and configured to transfer the driving force to the piston rod in order to drive the piston rod. The piston rod may be or may comprise, a lead screw or a toothed rod, for example. The piston rod may be operatively coupled to the force transfer subassembly such that the force transfer subassembly transfers the driving force to the piston rod.

In an embodiment, the assembly comprises a housing or body. The elements of the assembly, such as the piston rod or the force transfer subassembly, may be at least partially arranged within and are, preferably, retained in the housing. The housing may be an outer housing of the drug delivery device.

In an embodiment, the force transfer subassembly comprises a first force transfer member and a second force transfer member. The first force transfer member and the second force transfer member are expediently operatively coupled to each other, preferably in order to transfer the driving force to the piston rod. The force transfer members may be coupled to each other via a force-sensitive coupling. The force transfer members may be coupled via the force-sensitive coupling when the assembly is in the driving mode of operation. The force-sensitive coupling is preferably releasable. The force-sensitive coupling may be part of a protection or security mechanism which the assembly may comprise. This mechanism is expediently designed to prevent that an excessive force is transferred via the force transfer subassembly within the assembly.

In an embodiment, the force-sensitive coupling is arranged and configured to be released, particularly when an excessive force acts on the force-sensitive coupling. When the force-sensitive coupling is released or is being released, the assembly is switched from the driving mode of operation into a security mode of operation. The assembly may be designed to transfer a regular driving force which is less than or equal to a maximum acceptable driving force within the assembly. The excessive force may be greater than the maximum acceptable driving force or injection force. The maximum acceptable force may be a force which does not damage or deform components of the device and/or does not affect the dose accuracy or performance of the device. The excessive force may, in particular be greater than the maximum driving force which the assembly was designed for to be transferred within the assembly. Accordingly, the force transferrable with the force transfer subassembly may be limited, particularly to tolerable driving forces.

Consequently, if the excessive force acts on the force-sensitive coupling, the force-sensitive coupling is released thereby preventing an excessive force from being transferred within the assembly. Thus, the assembly may be reliably operated with forces smaller than the maximum driving force to dispense drug to a user. At greater forces, without the force-sensitive coupling, damage could occur, thereby rendering the operation of the device unreliable. Of course, drug delivery devices with an unreliable operation may have fatal, potentially lethal, consequences for the user when they are operated to dispense drug even though their dispense characteristics have been changed due to the excessive force, potentially even without being recognized by the user.

Excessive forces which may act on the force-sensitive coupling may, for example, occur when an outlet of the device is occluded and no medicament can be dispensed from the device without removing the occlusion. For example, a needle of the drug delivery device could be occluded, thereby considerably increasing, usually in an intolerable fashion, the force which would be required to dispense drug from the device. Another example of an excessive force is an impact force which may act on the drug delivery device, for example due to a user of the device dropping the device in, for example, a ready-to-dispense state.

In the security mode of operation, expediently, no force or no significant force is transferred to the piston rod. Thus, force-induced damages may be prevented.

In an embodiment, in the driving mode of operation, the first force transfer member and the second force transfer member are configured to be moved in a force transfer direction to transfer the driving force, particularly to the piston rod. The force transfer direction may be an axial direction. Before movement into the force transfer direction is enabled, a dose setting movement of the force transfer assembly, preferably including both force transfer members, may be performed from an initial position to a dose set position. The movement in the force transfer direction may be a movement counter to the dose setting direction. Consequently, when the dose is dispensed the force transfer subassembly may be moved from the dose set position towards the initial position.

Consequently, the force transfer subassembly may be moved during a dose setting operation and/or during a dose dispensing operation of the assembly. During each of these operations, the force transfer subassembly may be moved with respect to the housing. The force transfer subassembly may be designed to transfer the driving force to the piston rod when it is moved from the dose set position towards the initial position. During dose setting, the force transfer subassembly may be moved, particularly axially moved, relative to housing and piston rod. During dose dispensing, the force transfer subassembly may be moved axially together with the piston rod, particularly in the axial direction. Relative rotational movement between piston rod and force transfer subassembly may be allowed.

When the force-sensitive coupling is established, movement of the first force transfer member relative to the second force transfer member in the force transfer direction may be prevented. The force transfer members may be rigidly coupled, such as rotationally and/or axially, when the force-sensitive coupling is established. Preferably, relative movement along, e.g. in and/or counter to, the force transfer direction between the force transfer members is prevented in the driving mode of operation. In addition to relative movement along the force transfer direction, relative movement in a different direction, such as radial movement or azimuthal movement between the force transfer members may be prevented. In the driving mode of operation, the force transfer subassembly may act like a single part. Thus, in the dispensing mode of operation, a reliable operation of the assembly is guaranteed. In contrast thereto, when the force-sensitive coupling is released, movement of the first force transfer member relative to the second force transfer member, particular in the force transfer direction, is allowed. Movement of the transfer members relative to each other in a direction different from the force transfer direction may still be prevented. For example, if the force transfer direction is an axial direction, rotational movement may still be prevented and vice versa. When the first force transfer member moves with respect to the second force transfer member in the force transfer direction, the force required for this relative movement is expediently a lost force not being transferred to the piston rod. In order to switch the assembly into the security mode of operation, the first force transfer member may be moved with respect to the second force transfer member from an initial position, e.g. a position where the force-sensitive coupling is established, into an end position, e.g. a position where the force-sensitive coupling is released.

In an embodiment, the first force transfer member and/or the second force transfer member is guided, particularly with respect to the housing and/or along the force transfer direction. Movement in a different direction than in the force transfer direction may be prevented. For example, the first force transfer member and/or the second force transfer member may be axially guided. The first force transfer member and/or the second force transfer member may, consequently, be rotationally locked with respect to the housing. This guidance permits that the movement of the first force transfer member with respect to the second force transfer member is reliably guided. Consequently, the relative position of the transfer members is always well defined. Of course, alternatively to an axial guidance, the transfer members could also be rotationally guided with respect to the housing, particularly if the force transfer direction is or comprises a rotational direction.

In an embodiment, when the assembly is in the security mode of operation, the assembly may be switchable into the driving mode of operation. The force-sensitive coupling may be re-establishable for this purpose, e.g. by a relative movement between the force transfer members counter to the force transfer direction. Consequently, the assembly does not have to be disposed once it was switched from the driving mode of operation, which is the regular mode of operation, into the security mode of operation. Alternatively, the coupling may be non-re-establishable.

In an embodiment, the assembly is configured to stay in the security mode at least until a relative movement between the first and second transfer members counter to the force transfer direction is performed. By means of this movement, the force-sensitive coupling may be re-established. Particularly, if the assembly was once switched into the security mode and the reason why the assembly switched into the security mode, such as an occlusion or an impact on the ground, has been identified and eliminated, the device can be reused and does not have to be disposed of.

In an embodiment, the driving force which is to be transferred by the force transfer subassembly is a user-generated force. Consequently, the device may be a mechanically, particularly user-driven device as opposed to an electrically driven device, i.e. a device which uses electrical energy to drive the dispensing action. Still further, the driving force may be a force which is immediately exerted by the user and not by a force storage member to which the force was loaded before the dispensing begins, such as a spring, for example.

In an embodiment, the assembly comprises a dose member. The dose member may be movably retained in the housing. The dose member may be moved to set a dose of drug to be delivered and/or to dispense a drug to be delivered. For setting a dose, for example, the dose member may be moved from an initial position to a dose set position, e.g. proximally with respect to the housing. In the dose set position the device may be in a ready-to-dispense state. From the dose set position, the dose member may be moved back towards the initial position, e.g. distally with respect to the housing, for dispensing the set dose.

In an embodiment, the first force transfer member is arranged and configured to act as the dose member. The driving force may be exerted by the user on the dose member. Accordingly, a member of the force transfer subassembly may be provided for immediate user interaction. Consequently, as the excessive force may be an impact force acting on the dose member, particularly when the dose member is in the dose set position, the force protection mechanism provided by the force-sensitive coupling is arranged close to that element of the device which is manipulated for exerting a dispensing force. Consequently, the force-sensitive coupling may be the first interface which is exposed to the force when the force acts on the first force transfer member. Elements which are arranged further down the force path within the assembly are thus not exposed to the excessive force as the excessive force does not have any significant influence on the internal parts once the force-sensitive coupling is released.

In an embodiment, the second force transfer member is retained within the housing. The second force transfer member may be inaccessible from outside of the housing. The first force transfer member may be accessible from outside of the housing. Expediently, only a part of the first force transfer member is retained within the housing, particularly when the force transfer subassembly is in its dose set position and/or in its initial position. The first force transfer member may thus be accessible for the user of the device and can be manipulated by the user. The function of the first force transfer member as the dose member is facilitated in this way.

In an embodiment, the second force transfer member is a drive member. The second force transfer member may be arranged and configured to act on the piston rod to drive movement of the piston rod. The second force transfer member may interact immediately with the piston rod. Particularly, the second force transfer member may be the last element which transfers force to the piston rod in the force path from the dose member to the piston rod.

In an embodiment, the assembly is configured to provide a feedback to the user, e.g. about the mode of operation of the assembly. For example, the assembly may be configured to provide a feedback to the user that the assembly is being switched into the security mode or is in the security mode of operation. The feedback which is provided may be or may comprise audible, tactile and/or visual feedback.

In an embodiment, the assembly comprises an indicator window which is, preferably, visible from outside of the assembly. The window is provided to display information, particularly to a user. Expediently, the information displayed in the indicator window is different in the driving mode of operation and in the security mode of operation. Accordingly, a visual feedback for the mode of operation which the device or the assembly is in may be provided in the indicator window. It is particularly advantageous if the first force transfer member defines the indicator window. The indicator window may be provided in that part of the first force transfer member which is arranged outside of the housing. A separate window in the housing may then be dispensed with.

In the security mode of operation, a surface of the second force transfer member may be displayed in the indicator window. The surface of the drive member may be coloured or marked in a different manner to emphasize the indicated information. The surface of the drive member may be brought into a position to be displayed by the indicator window by means of the relative movement between the first force transfer member and the second force transfer member which is performed to switch the assembly from the dispensing mode of operation into the security mode of operation. In the dispensing mode of operation, the surface of the second force transfer member is preferably not visible through the window or that portion of the force transfer member which is visible in the window is recognizably different from the one which is visible when the assembly is in the security mode of operation.

In an embodiment, the first force transfer member and the second force transfer member are positively connected. The force transfer members may be connected via a positive fit. The connection between the first force transfer member and the second force transfer member may establish the force-sensitive coupling.

In an embodiment, the first force transfer member and the second force transfer member are engaged with one another to establish the force-sensitive coupling. The engagement may be releasable to release the force-sensitive coupling. The engagement is, expediently, stable enough such that the driving force may be transferred via the force transfer subassembly.

In an embodiment, the engagement between the first force transfer member and the second force transfer member is configured to provide one or both of the following feedbacks when it is released: audible feedback, tactile feedback.

A particularly advantageous embodiment which is proposed relates to an assembly for a drug delivery device, comprising:
  a piston rod,
  a force transfer subassembly, the force transfer subassembly being arranged and configured, in a driving mode of operation of the assembly, to transfer a driving force to the piston rod in order to drive the piston rod, the force transfer subassembly comprising
  a first force transfer member, and
  a second force transfer member, wherein
  the first force transfer member and the second force transfer member are operatively coupled to each other via a force-sensitive coupling to transfer the driving force to the piston rod, and wherein, when an excessive force acts on the force-sensitive coupling, the force-sensitive coupling is arranged and configured to be released in order to switch the assembly from the driving mode of operation into a security mode of operation.

The advantages of this embodiment become readily apparent from the description above and the following description.

Further features, refinements and advantageous embodiments of the present disclosure become apparent from the following description of the exemplary embodiments in conjunction with the appended figures.

Figure 1:
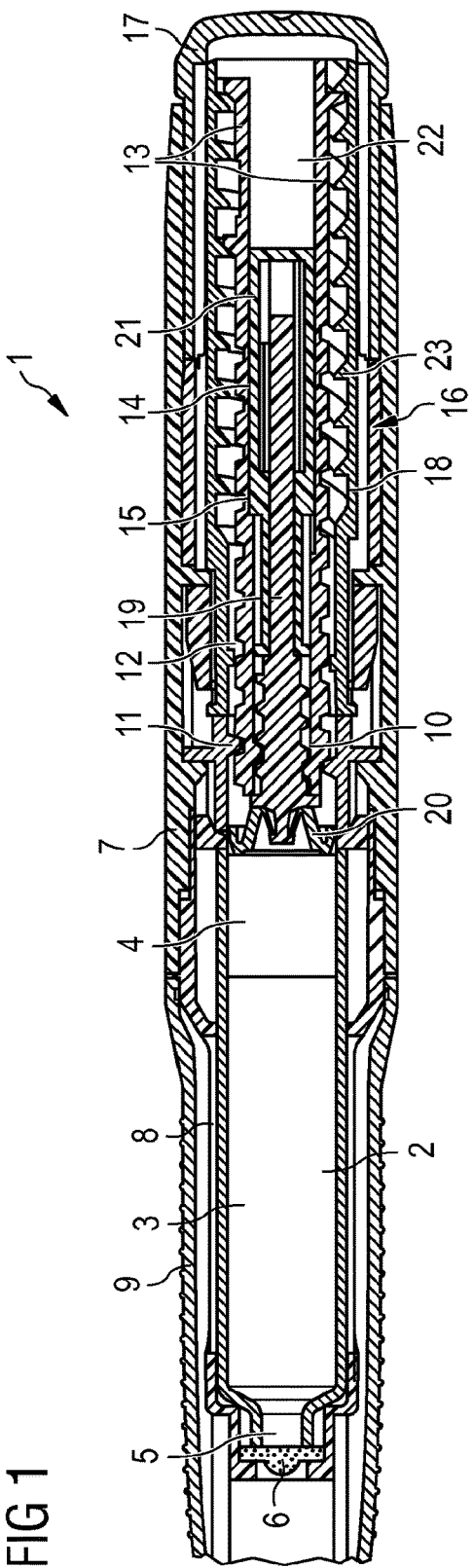
FIG. 1 shows an exemplary embodiment of a drug delivery device on the basis of a schematic sectional view.

In the figures, identical elements, identically acting elements and elements of the same kinds are designated with the same reference numerals. Furthermore, for a better illustration of the disclosed concepts, certain features of the depicted elements may be depicted in an exaggerated fashion and not true to scale in order to facilitate explanation of the disclosed concepts.

FIG. 1 shows, on the basis of a schematic sectional view, an exemplary embodiment of a drug delivery device 1. The drug delivery device 1 may be an injection device. The drug delivery device 1 may be a pen-type device. The drug delivery device 1 may be a disposable or a reusable device. The drug delivery device 1 may be a fixed dose device. Alternatively, the present concept is also applicable for variable dose devices where the size of the dose to be set can be varied by the user, whereas in fixed dose devices the size of the dose may not be varied by the user but is present by the device design.

It should be noted that the above-mentioned concept with the attenuation member should not be construed to be limited to the particular drug delivery device 1 described herein below although it may be particularly advantageous for this device.

The drug delivery device 1 comprises a cartridge 2. Within the cartridge a drug 3, which may be a liquid drug, is retained. Furthermore, a bung 4 is movably retained in the cartridge 2. The bung 4 seals the cartridge 2 proximally to prevent drug 3 from dripping out of the cartridge 2. If the bung 4 is driven in the distal direction with respect to the cartridge, drug may be dispensed from the cartridge through an outlet 5 of the cartridge, provided that fluid communication between the interior of the cartridge and the exterior is provided, for example by means of a needle unit which pierces membrane 6 which seals the outlet 5.

"Distal" as used herein refers to the direction or the end of an element facing the dispensing end of the drug delivery device and "proximal" as used herein refers to the direction or the end of an element facing away from the dispensing end of the drug delivery device.

The term "drug", as used herein, preferably means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser- Ser-Gly-Ala-Pro-Pro-Pro-Ser-NH2.

Exendin-4 derivatives are for example selected from the following list of compounds:

H-(Lys)4-des Pro36, des Pro37 Exendin-4(1-39)-NH2,
H-(Lys)5-des Pro36, des Pro37 Exendin-4(1-39)-NH2,
des Pro36 Exendin-4(1-39),
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39), wherein the group -Lys6-NH2 may be bound to the C-terminus of the Exendin-4 derivative;

or an Exendin-4 derivative of the sequence des Pro36 Exendin-4(1-39)-Lys6-NH2 (AVE0010),
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2, H-Asn-(Glu)5-des Pro36, Pro37, Pro38 [Met(O)14, Asp28] Exendin-4(1-39)-NH2, des Pro36, Pro37, Pro38 [Met(O)14, Asp28] Exendin-4 (1-39)-(Lys)6-NH2, H-(Lys)6-des Pro36, Pro37, Pro38 [Met(O)14, Asp28] Exendin-4(1-39)-(Lys)6-NH2, H-Asn-(Glu)5 des Pro36, Pro37, Pro38 [Met(O)14, Asp28] Exendin-4(1-39)-(Lys)6-NH2, H-Lys6-des Pro36 [Met(O)14, Trp(O2)25, Asp28] Exendin-4(1-39)-Lys6-NH2, H-des Asp28 Pro36, Pro37, Pro38 [Met(O)14, Trp(O2)25] Exendin-4(1-39)-NH2, H-(Lys)6-des Pro36, Pro37, Pro38 [Met(O)14, Asp28] Exendin-4(1-39)-NH2, H-Asn-(Glu)5-des Pro36, Pro37, Pro38 [Met(O)14, Trp(O2)25, Asp28] Exendin-4(1-39)-NH2, des Pro36, Pro37, Pro38 [Met(O)14, Trp(O2)25, Asp28] Exendin-4(1-39)-(Lys)6-NH2, H-(Lys)6-des Pro36, Pro37, Pro38 [Met(O)14, Trp(O2) 25, Asp28] Exendin-4(S1-39)-(Lys)6-NH2, H-Asn-(Glu)5-des Pro36, Pro37, Pro38 [Met(O)14, Trp (O2)25, Asp28] Exendin-4(1-39)-(Lys)6-NH2;

or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region ($C_H$) and the variable region ($V_H$). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H—H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

The drug delivery device 1 further comprises a drive mechanism which is arranged and operable to drive movement of the bung in the distal direction with respect to the cartridge to dispense drug 3 from the device. The device 1 described herein is similar to the one described in WO 2008/058665 A1, the disclosure content of which is incorporated by reference herewith into the present application as far as the design of the device and, in particular, of its drive mechanism, is concerned. Elements of the drive mechanism may be housed in a body or housing 7 of the drug delivery device 1. The cartridge may be connected to the body 7, either directly or, as depicted, by means of a cartridge retainer or cartridge holder 8. The cartridge holder 8 may be, releasably or permanently, coupled to the body 7.

The drug delivery device further comprises a cap 9. The cap 9 is releasably attachable to the body 7 or the cartridge holder 8. The cap 9 is suitable to cover the dispensing end of the drug delivery device 1, preferably the cartridge 2 or the cartridge holder 8. For preparing the device for drug delivery, the cap may be removed and a needle unit may be attached to the outlet to provide fluid communication between the interior of the cartridge 2 and the outside.

The drug delivery device 1 further comprises a piston rod 10 which is arranged to transfer a driving force to the bung 4. The piston rod 10 comprises a main body 14. The piston rod 10, in the present case a lead screw, may be threadedly engaged with a nut member 11. The nut member 11 is expediently axially and rotationally secured within the body 7. Thus, if the piston rod 10 is rotated, on account of its threaded engagement with the nut member, it is displaced axially with respect to the body and, consequently, advanced within the cartridge 2 to dispense drug 3 from the cartridge 2.

The piston rod 10, particularly the main body 14, is provided with a piston rod thread 12. By means of the thread 12, the threaded engagement between piston rod 10 and nut member 11 can be established. The piston rod thread 12 is arranged in a distal section of the main body 14.

In a proximal section of the piston rod 10, one or more of elastically displaceable features 13 are arranged. The elastically displaceable features 13 are elastically deformable and may be formed integrally with the main body 14 of the piston rod 10, for example. The elastically displaceable features 13 may alternatively be resiliently mounted to the main body 14. However, with respect to manufacturing costs, an integral formation is expedient. The main body 14 is expediently rigid, whereas the features 13 are flexible, on account of cut-outs in the main body 14. The features 13 extend axially. The features 13 can be embodied as axially extending fingers.

The main body 14 further defines a hollow interior 15 wherein components of the device or of the piston rod 10 can be arranged. The piston rod may be a multi-part component. Alternatively, the piston rod may be a single part.

The drug delivery device 1 comprises a drive member 16. The drive member may be a drive sleeve. The drive member 16 may be designed to transfer a driving force from the user to the piston rod 10. For this purpose, the drive member 16 may be movable in the proximal direction with respect to the body 7 for setting a dose and in the distal direction for delivering the dose. The distal movement may be transferred or converted into movement of the piston rod 10. During the proximal movement, the piston rod 10 is expediently stationary. The drive member 16 may be rotationally secured to the body such that no relative rotation may be allowed. The piston rod 10, in particular the proximal section with the elastically displaceable features is retained in and preferably in contact with the drive member 16.

The device further comprises a dose member 17. The dose member 17 is operable by a user and movable with respect to the body 7 in the proximal direction to set a dose and in the distal direction for delivering the set dose. In a dispensing mode of operation of the drug delivery device, the dose member is rotationally and axially locked to the drive member, i.e. axial movement of the dose member with respect to the body is permitted, whereas rotational relative movement is prevented.

The drive member 16 comprises a drive member thread 18. The drive member thread may be a female thread and/or a helical thread. The drive member thread 18 is disposed along an inner surface of the drive member 1. The drive member thread 18 may be defined by a protrusion 23, which preferably extends along the interior of the drive member 16. The drive member thread 18 is arranged to interact with the elastically displaceable features 13 during operation of the device 1. The protrusion 23 is arranged to interact with the elastically displaceable features 13 during operation of the device 1.

FIG. 1 shows a drug delivery device 1 with a full cartridge 2, i.e. no dose has been delivered yet. As doses of drug are delivered from the cartridge 2 the piston rod 10 is successively moved distally with respect to the body 7 and the drive member 16.

During dose setting, the piston rod 10 is axially and rotationally secured such that when the drive member 16 is moved proximally into a dose set position. During this movement of the drive member 16 the elastically displaceable features 13 of the piston rod 10 are deflected radially inwardly and slide out of engagement with the drive member thread 18 and are thus displaced relative to the main body 14. The deflection is achieved by the section of the protrusion 23 defining the drive member thread 18, while the section abuts the respective elastically displaceable feature 13. The dose setting travel of the drive member 16 just exceeds the length of one pitch of the drive member thread 18. Thus, in the dose set position, the elastically displaceable features of the piston rod 10 re-engage with the drive member thread 18 as they move back towards the undisplaced position on account of the elastic restoring force. The movement towards the undisplaced position may be stopped when the respective elastically displaceable feature hits the drive member 16 and provides an audible and/or tactile feedback that the dose has been set. For dispensing the dose, the drive member is moved in the distal direction with respect to the body 7 towards the position it had before the setting action was performed, i.e. towards the position depicted in FIG. 1. During the dispensing action, the drive member thread 18 is used to rotate the piston rod 10. Particularly, distal facing surfaces of the protrusion 23, engage proximally facing surfaces of the elastically displaceable features 13. Thus, during dose delivery, no elastic displacement of the features 13 is caused, but the piston rod 10 is rotated and thus advanced through the nut member 11. The elastically displaceable features are used to create feedback during dose setting and to drive movement of the piston rod during dose dispensing.

Figure 2:
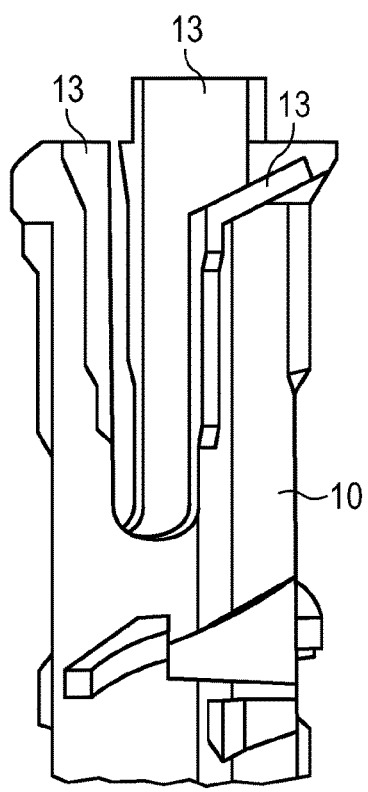
FIG. 2 shows a section of a piston rod of the drug delivery device.
Figure 3:
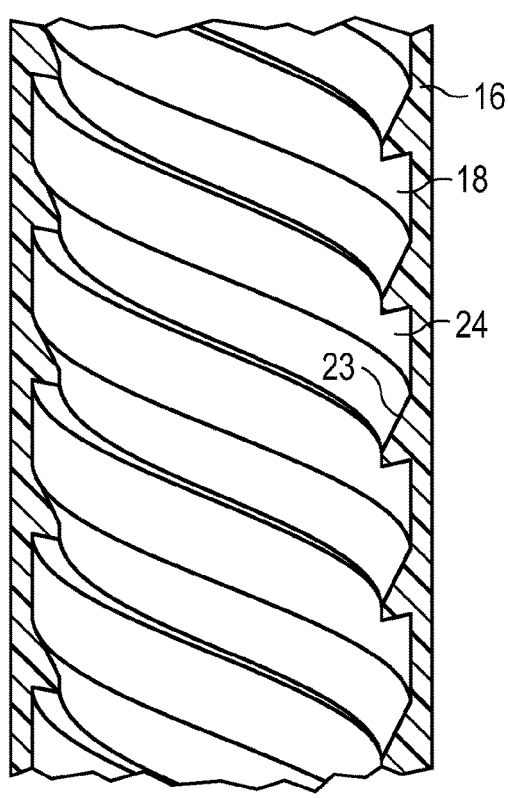
FIG. 3 shows, on the basis of a schematic sectional view, a section of a drive member of the drug delivery device.
Figure 4:
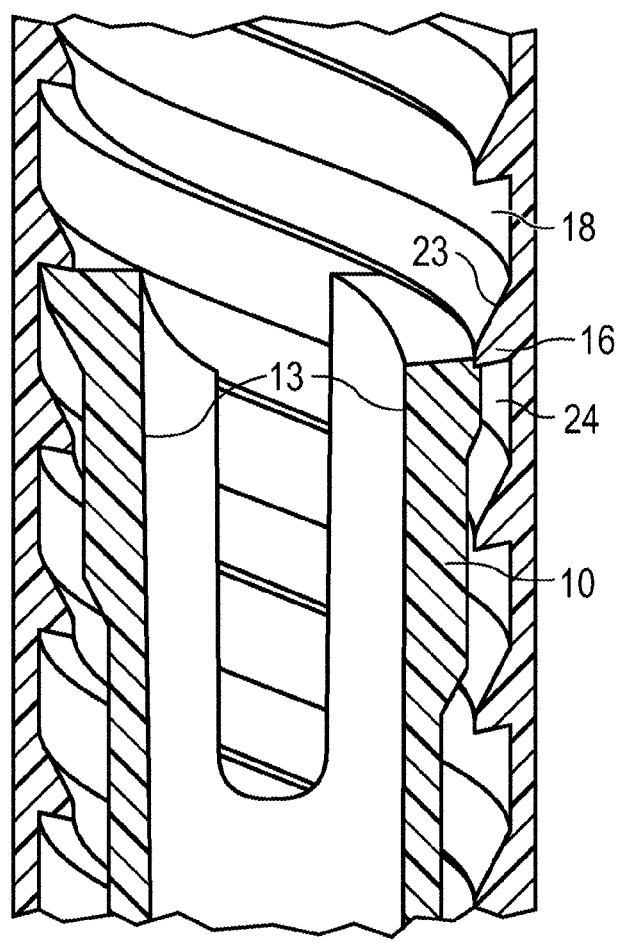
FIG. 4 shows, on the basis of a schematic sectional view, the interaction between the drive member and the piston rod of FIGS. 2 and 3.

FIG. 4 shows a situation near the end of a dose setting operation where the right elastically displaceable feature 13 is still radially inwardly displaced by a section of the protrusion 23, i.e. a position shortly before the dose setting action has been completed and before the feature 13 engages the space 24, i.e. the next winding of the thread 18. FIG. 2 shows the proximal section of the piston rod 10 and FIG. 3 shows a section of the drive member 16.

During dose delivery, the drive member 16 is moved distally with respect to the body 7 and the elastically displaceable features 13, particularly a proximally facing surface thereof, interact with the drive member thread 18, particularly a distal facing surface of the protrusion defining the thread, such that, as the drive member 16 is rotationally locked to the body 7, the piston rod 10 is caused to rotate and, on account of the threaded engagement with the nut member 11, caused to advance in the distal direction with respect to the body 7. Consequently, the drive member thread 18 is designed as a non self-locking thread which causes the piston rod to rotate when it is subject to an axial load. The threads 18 of the drive member and 12 of the piston rod may have opposite hands. During dose delivery the piston rod 10 is advanced by a distance that corresponds to the relationship between the leads of the piston rod thread 12 and the drive member thread 18 which, of course, may be different. The piston rod thread 12 lead is less than the one of the drive member thread 18. The mechanical advantage may be 3.2:1 or, if some lost motion of the drive member is accounted for which does not drive the piston rod 10, 4:1.

The piston rod 10 further comprises an adjusting member 19. The adjusting member is retained within the interior 15 of the main body 14. The adjusting member 19 is threadedly engaged with the main body 14 of the piston rod 10, particularly with a thread in the region of the distal end of the main body. By means of the adjusting member 19 a length of the piston rod 10 can be varied. A distal end of the adjusting member may be provided with a bearing member 20 which is designed to abut the bung 4 to advance the bung when the piston rod 10 is moved distally. The threaded engagement between the adjusting member 19 and the main body 14 can be designed such that it is a self-locking, i.e. no relative rotation occurs when the adjusting member 19 or the main body 14 is subject to an axial load. Accordingly, it is avoided that the adjusting member 19 rotates with respect to the main body 14 when the piston rod advances axially. By means of the adjusting member the length of the piston rod can be varied. Consequently, a gap between the piston rod and the bung which gap could be present if the piston rod had a fixed length during the assembling of the device may be reduced or even eliminated by varying the length of the piston rod 10 by means of the adjusting member 19. Thus, already the first dose of drug delivered form a new cartridge by the drug delivery device 1 can be used by the user and no priming or prime shot is necessary to remove tolerances in the drug delivery device.

The adjusting member 19 may be rotationally locked with respect to a locking member 21. Locking member 21 may be retained within the main body 14 of the piston rod 10. The locking member 21 may be used during assembly of the device to rotate the adjusting member and thus to vary the length of the piston rod 10. The locking member may be accessible from the proximal end of the piston rod 10 during assembly, e.g. before the dose member is secured to the drive member. Once the desired length of the piston rod has been reached, the locking member 21 may be moved axially with respect to the main body 14 and the adjusting member 19 and, during this movement, be rotationally secured with respect to the main body 14 and also axially secured against movement in the proximal and/or distal direction, for example by a snap-fit engagement, with respect to the adjusting member 19. The rotational locking between the locking member 21 and the main body 14 may be achieved by splines provided on the locking member and slots on an interior surface of the main body in a section of the main body, the splines engaging the slots when the locking member 21 is moved distally with respect to the main body 14. The proximal end section 22 of the interior 15 of the main body 14 may be open, as depicted, or closed.

If the adjusting member 19 is dispensed with, the piston rod 10 may be a single part—if applicable with a separate bearing 20.

The device depicted in FIG. 1 is fully operable to set and dispense doses of the drug 3. In addition to the functions of the drug delivery device already described above, the drug delivery device comprises a security or protection mechanism. This mechanism ensures that excessive forces do not reach interior components of the device such as piston rod 10, bung 4 or drug 3. Consequently, damage or inaccurate operation of the device may be prevented by the security mechanism. Embodiments of the security mechanism were already described in the general part of the description to which it is also referenced in the present context.

Figure 5:
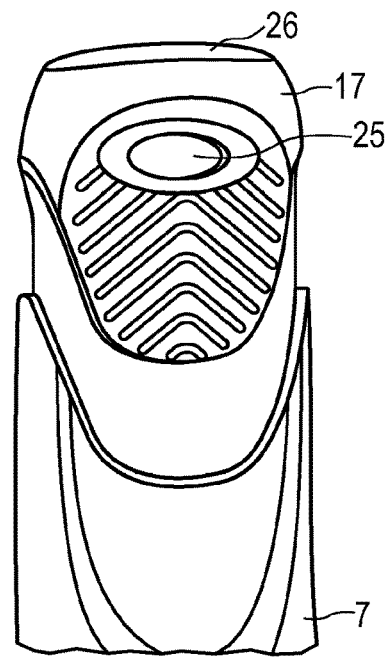
FIG. 5 shows the drug delivery device in a driving mode of operation when a dose was set.
Figure 6:
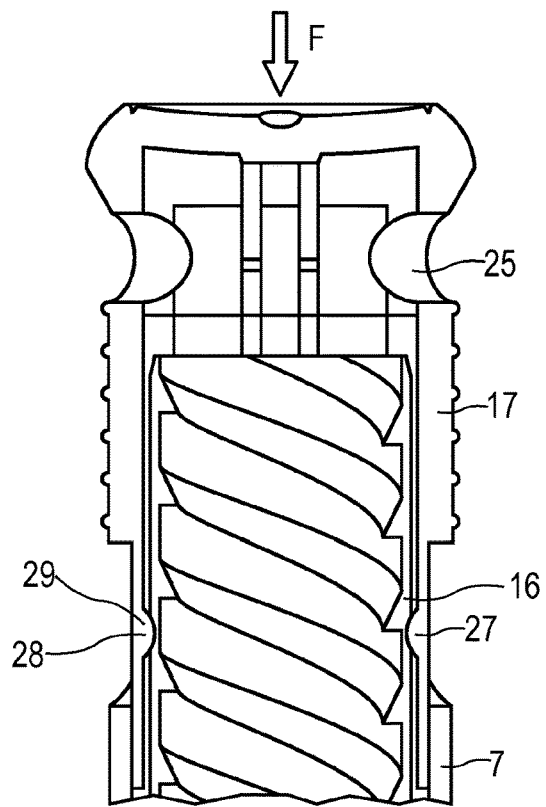
FIG. 6 shows the associated sectional view.
Figure 7:
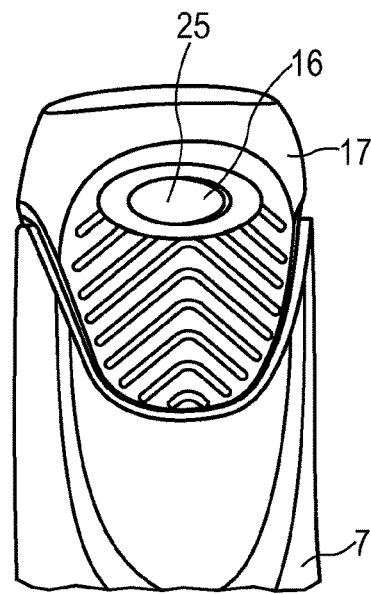
FIG. 7 shows, on the basis of a schematic side view, the device in a security mode of operation.
Figure 8:
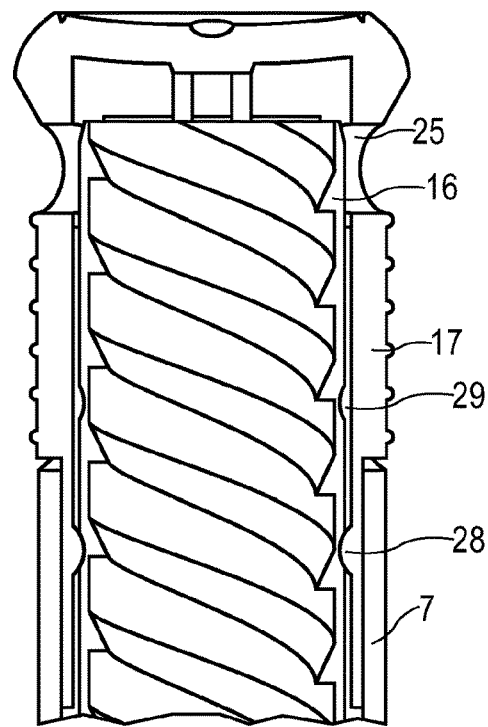
FIG. 8 shows the associated sectional view.

In the following text, an exemplary embodiment of a security mechanism is described in conjunction with FIGS. 5 to 8. Therein, FIG. 5 shows the drug delivery device in a driving mode of operation when a dose was set. FIG. 6 shows the associated sectional view. FIG. 7 shows, on the basis of a schematic side view, the device in a security mode of operation. FIG. 8 shows the associated sectional view.

For the security mechanism a force transfer subassembly is provided which comprises a first force transfer member and a second force transfer member. These members transfer a driving force through the device in a driving mode of operation and, due to a force-sensitive coupling established between them, prevent an excessive force from being transferred in the device to the bung or the drug when the device is switched in a security mode of operation from the driving mode.

The described exemplary embodiment of the force transfer subassembly comprising the first and the second force transfer members is described below using the dose member 17 as the first force transfer member and the drive member 16 as the second force transfer member. However, it will be readily apparent to one of skill in the art that other members which are transferring a force through a device could be used for a force transfer subassembly, especially in other drug delivery devices for which the disclosed concepts may also apply. However, for the currently described device using dose member 17 and drive member 16 as first and second force transfer members, respectively, is particularly advantageous. Accordingly, references above and below to the dose member 17 and the drive member 16 may be regarded as references to the first force transfer member and the second force transfer member, respectively.

FIG. 5 shows the drug delivery device 1 in a dose set position, i.e. a position in which the dose member 17 has been moved in the proximal direction with respect to the housing from an initial position to a dose set position in order to set a dose. The dose member 17 comprises an indicator window 25 which is provided in a side surface of the dose member, i.e. a surface extending away, particularly in the distal direction, from an end surface or actuation surface 26, which is designed to be contacted by a user's finger, e.g. the thumb, when moving the dose member 17 into the distal direction with respect to the housing for delivering a set dose. The dose member may, consequently, be a dose button.

The dose member 17 is designed as a hollow component which, in its interior, has received at least a part of the drive member 16. As can be gathered from FIG. 6, the drive member 16 in the dose set position, is spaced apart from the indicator window 25 and not visible within the indicator window.

Furthermore, the drive member 16 and the dose member 17 are coupled to each other via the force-sensitive coupling 27. The coupling 27 is designed such that during regular operation of the device, i.e. in the dispensing mode where setting and dispensing movements can be performed, the dose member and the drive member are coupled. Particularly, they are coupled in the axial direction, i.e. that direction in which forces are transferred by means of the force transfer subassembly. Within body 7, dose member 17 and drive member 16 may be axially guided, i.e. they are prevented from rotation with respect to the body. A guide slot and a cooperating protrusion may be provided for this purpose. In the dispensing mode of operation of the drug delivery device 1, the dose member 17 and the drive member 16 act as a single part. The coupling 27 is preferably so stable that regularly applied forces for dose setting and/or dose delivery, i.e. setting forces and dispensing forces, are reliably transferred via the force transfer subassembly comprising drive member 16 and dose member 17.

If the device is in the dose set position as depicted in FIG. 1, there are a plurality of potential unpredictable events which can occur and which may significantly increase the force acting on the device, e.g. the force which would be required to inject or eject medicament from the cartridge 2, potentially to an extent which negatively affects the dose accuracy of the device or even damages the device. One of these events is a blocked needle. The force which would be required to dispense liquid from the blocked needle may be so high that interior components would be seriously damaged if the force was tried to be transferred within the device. Another possible event is that the device is dropped on the floor in the dose set position of the dose member. When this happens, the actuation surface 26 may hit the floor with a significant force acting on the dose member 16, the force also being so high that it potentially damages interior components of the device or affects the dose accuracy.

In order to prevent negative effects of this kind, the coupling 27 is designed to be a force-sensitive coupling. The force-sensitive coupling is designed such that it transfers regularly occurring forces during setting and dispensing reliably but is released once an excessive force, such as an impact force when the device hits the ground or a force being exerted by a user when the needle is blocked, acts on the coupling. For this purpose, an exemplary embodiment of the coupling 27 comprises a protrusion 28 provided at the dose member 17. The protrusion extends radially inwardly into the interior of the dose member 17. The protrusion 28 may be formed circumferentially, preferably ring-like. The coupling 27 further comprises an indentation 29. The indentation 29 is provided at the drive member 16. The indentation extends particularly in the radial direction. The indentation 29 may be provided on an outer surface of the drive sleeve 16. As long as the protrusion 28 engages the indentation 29, the force transfer subassembly transfers forces within the device and particularly it transfers forces directed into the distal axial direction to the piston rod. Usually driving forces are higher than setting forces so that it is particularly expedient to design the force-sensitive coupling to at least transfer regular driving forces within the device.

From the position depicted in FIG. 6, a distally acting force F may be exerted by a user. If the device operates normally and the force F is less than the maximum acceptable driving force, this force is transferred to the piston rod 10 and the bung 4 within the cartridge 2 and results in a dose of drug 3 being dispensed from the device 1. If, however, one of the above events occurs, the force-sensitive coupling 27 is released when the user applies an excessive force, thereby permitting relative movement between the dose member 17 and the drive member 16. In order to release the coupling, the drive member and/or the dose member may be slightly deformed, particularly in a radial direction and/or elastically. Thereby the engagement between the drive member and the dose member may be released, particularly by the protrusion 28 disengaging the indentation 29. The release may generate an audible noise and/or a vibration which the user may experience. This informs the user that the device does not operate in a normal way and is being switched into the security mode of operation. After the engagement has been released, the dose member 17 is axially displaced in the distal direction with respect to the drive member 16 without the drive member 16 being displaced in the distal direction with respect to the body 7. Consequently, the force F is not transferred to the drive member, i.e. the second force transfer member, and consequently not to the piston rod 10. Rather, this force is only used for the relative movement between dose member 17 and drive member 16.

The maximum admissible dispensing force which may be transferred via the force-sensitive coupling can be adjusted by means of the interfaces between the protrusion 28 and the indentation 29, for example by the radial extension of the protrusion and/or the indentation. Relative movement between the dose member and the drive member in the dose setting direction may be prevented in the driving mode. That is to say, the force-sensitive coupling may be designed as non-releasable when the force transfer subassembly is moved for setting a dose in the dose setting direction. This prevents that the device can be easily disassembled by the user. The proximal face of the protrusion may be steeper than the distal face for this purpose (not explicitly illustrated). It is, of course, readily apparent to a person of skill that the protrusion may also be arranged on the drive member 16 and the indentation on the dose member 17. Further, other force-sensitive couplings may readily apparent to a person of skill depending on in what kind of device the force-sensitive coupling is applied for.

FIGS. 7 and 8 show the drug delivery device with the dose member 17 having resumed its end position with respect to drive member 16 after having performed the relative movement. In this position, an outer surface of the drive member 16 is displayed in the window. The drive member 16 is preferably coloured, e.g. red, such that a user may easily identify that the device is in the security mode of operation and that the dose he tried to deliver was not properly delivered, for example, due to a blocked needle. Accordingly, various feedbacks are provided to the user that the device does not function properly in case an excessive force is applied to the dose member 17.

Thus, by means of the proposed security mechanism it is ensured that the device components are not getting damaged and also that the user is informed that the device does not function properly.

The coupling 27 may be designed to be re-establishable, for example by proximal movement of the dose member 17 with respect to the drive member 16. After a subsequent dose setting movement has been performed, this again results in a dose set position which is depicted in FIG. 6. If the cause for the switching into the security mode, for example the blocked needle, is removed, the device may be used normally. Alternatively, in case the coupling is not re-establishable the device may be locked out and not be used again, as it has functioned improperly only once.

Although the security mechanism has been described in detail herein only with respect to the drug delivery device described in conjunction with FIGS. 1 through 4, it should be readily apparent to a person of skill that the disclosed concept could also apply to other devices, e.g. devices using a toothed rod instead of a lead screw as the piston rod or employing different drive mechanisms. Particularly, it need not be an axial force which is transferred and used to release the force-sensitive coupling. It could also be a rotational force and/or a force comprising rotational and axial components. Some examples suitable for other mechanisms are disclosed in the general part of the description to which it is referred in this regard.

The scope of protection of the invention is not limited to the examples given hereinabove. The invention is embodied in each novel characteristic and each combination of characteristics, which particularly includes every combination of any features which are stated in the claims, even if this feature or this combination of features is not explicitly stated in the claims or in the examples.

REFERENCE NUMERALS 1 drug delivery device
2 cartridge
3 drug
4 bung
5 outlet
6 membrane
7 body
8 cartridge holder
9 cap
10 piston rod
11 nut member
12 piston rod thread
13 elastically displaceable feature
14 main body
15 interior
16 drive member
17 dose member
18 drive member thread
19 adjusting member
20 bearing member
21 locking member
22 proximal end section
23 protrusion
24 space
25 indicator window
26 surface
27 coupling
28 protrusion
29 indentation
F force

The invention claimed is:

1. An assembly for a drug delivery device, comprising:
a piston rod; and
a force transfer subassembly, the force transfer subassembly being configured, in a driving mode of operation of the assembly, to transfer a driving force to the piston rod in order to drive the piston rod, the force transfer subassembly comprising:
a first force transfer member, and
a second force transfer member,
wherein the first force transfer member and the second force transfer member are operatively coupled to each other via a force-sensitive coupling, the force-sensitive coupling is configured to transfer the driving force to the piston rod, and wherein the force-sensitive coupling is configured to be released when an excessive force acts on the force-sensitive coupling to switch the assembly from the driving mode of operation into a security mode of operation.

2. The assembly according to claim 1, wherein, in the driving mode of operation, the first force transfer member and the second force transfer member are configured to be moved in a force transfer direction to transfer the driving force to the piston rod, and wherein, when the force-sensitive coupling is established, movement of the first force transfer member relative to the second force transfer member in the force transfer direction is prevented, whereas, when the force-sensitive coupling is released, movement of the first force transfer member relative to the second force transfer member in the force transfer direction is allowed.

3. The assembly according to claim 2, wherein the first and second force transfer members are configured such that when the first force transfer member moves with respect to the second force transfer member in the force transfer direction, the force required for the relative movement is a lost force not being transferred to the piston rod.

4. The assembly according to claim 2, wherein the force transfer direction is an axial direction.

5. The assembly according to claim 1, wherein the driving force is a user generated force.

6. The assembly according to claim 1, wherein the first force transfer member and the second force transfer member are axially guided.

7. The assembly according to claim 1, further comprising a housing, wherein the second force transfer member is retained within the housing and the first force transfer member is accessible from outside of the housing, and wherein the first force transfer member is configured to act as a dose member which can be manipulated by a user.

8. The assembly according to claim 1, wherein the second force transfer member is a drive member configured to act on the piston rod to drive movement of the piston rod.

9. The assembly according to claim 1, wherein the assembly is configured to provide a feedback to the user that the assembly is being switched into the security mode of operation and/or is in the security mode of operation.

10. The assembly according to claim 1, wherein the first force transfer member defines an indicator window which is visible from outside of the assembly and wherein information displayed in the indicator window is different in the driving mode of operation and in the security mode of operation.

11. The assembly according to claim 10, wherein, in the security mode of operation, a surface of the second force transfer member is displayed in the indicator window.

12. The assembly according to claim 1, wherein the first force transfer member and the second force transfer member are engaged with one another to establish the force-sensitive coupling, the engagement being releasable to release the force-sensitive coupling.

13. The assembly according to claim 12, wherein the engagement is configured to provide one or both of the following feedbacks when it is released: audible feedback and tactile feedback.

14. The assembly according to claim 1, wherein the assembly, when in the security mode of operation, is switchable into the driving mode of operation.

15. A drug delivery device comprising: a housing;
an assembly at least partially disposed in the housing, the assembly comprising:
a piston rod, and
a force transfer subassembly, the force transfer subassembly being configured, in a driving mode of operation of the assembly, to transfer a driving force to the piston rod in order to drive the piston rod, the force transfer subassembly comprising:
a first force transfer member, and
a second force transfer member,
wherein the first force transfer member and the second force transfer member are operatively coupled to each other via a force-sensitive coupling, the force-sensitivity coupling is configured to transfer the driving force to the piston rod, and wherein the force-sensitive coupling is configured to be released, when an excessive force acts on the force-sensitive coupling, wherein releasing the force-sensitive coupling switches the assembly from the driving mode of operation into a security mode of operation; and
a reservoir at least partially disposed in the housing, the reservoir comprising a drug to be delivered by the device.

16. The drug delivery device of claim 15, wherein the reservoir comprises a pharmaceutically active compound.

17. A method comprising:
applying a force to a proximal end of a drug delivery device, first and second force transfer members of a force-sensitive coupling of the drug delivery device being in a driving mode of operation, the force-sensitive coupling transferring the force to a piston rod of the drug delivery device to drive the delivery of a drug from the drug delivery device, and
increasing the applied force above a threshold value, the increased force decoupling the first and second force transfer members and switching the drug delivery device from the driving mode of operation into a security mode of operation, thereby preventing the applied force from being transferred to the piston rod.

* * * * *